(12) United States Patent
Sia

(10) Patent No.: US 10,207,050 B2
(45) Date of Patent: Feb. 19, 2019

(54) COMPUTER-IMPLEMENTED METHOD FOR CONTROLLING DISPENSING OF A BIOLOGICALLY ACTIVE AGENT; COMPUTER SYSTEM AND SOFTWARE THEREOF

(71) Applicant: SINGAPORE HEALTH SERVICES PTE LTD, Singapore (SG)

(72) Inventor: Tiong Heng Alex Sia, Singapore (SG)

(73) Assignee: Singapore Health Services Pte. Ltd., Singapore (SG)

( * ) Notice: Subject to any disclaimer, the term of this patent is extended or adjusted under 35 U.S.C. 154(b) by 801 days.

(21) Appl. No.: 14/363,310

(22) PCT Filed: Dec. 7, 2012

(86) PCT No.: PCT/SG2012/000460
§ 371 (c)(1),
(2) Date: Jun. 6, 2014

(87) PCT Pub. No.: WO2013/085466
PCT Pub. Date: Jun. 13, 2013

(65) Prior Publication Data
US 2014/0316371 A1    Oct. 23, 2014

Related U.S. Application Data

(60) Provisional application No. 61/567,892, filed on Dec. 7, 2011.

(51) Int. Cl.
*A61M 5/172* (2006.01)
*A61M 19/00* (2006.01)
(Continued)

(52) U.S. Cl.
CPC ........ *A61M 5/172* (2013.01); *A61M 5/16877* (2013.01); *A61M 19/00* (2013.01);
(Continued)

(58) Field of Classification Search
CPC ................ A61M 5/172; A61M 5/1723; A61M 2005/1726; A61M 5/16877; A61M 5/168; A61M 19/00; A61M 2005/14208
See application file for complete search history.

(56) References Cited

U.S. PATENT DOCUMENTS 3,923,060 A     12/1975  Ellinwood, Jr.
4,000,741 A *   1/1977   Binard ............... A61B 17/3401
                                                    604/121
(Continued)

FOREIGN PATENT DOCUMENTS

EP    1 082 056 B1    11/2007

OTHER PUBLICATIONS

Extended European Search Report, dated Aug. 6, 2015, for corresponding European Application No. 12855068.8-1952 / 2788064, 4 pages.
(Continued)

*Primary Examiner* — Bradley J Osinski
*Assistant Examiner* — Nilay Shah
(74) *Attorney, Agent, or Firm* — Seed IP Law Group LLP

(57) ABSTRACT

There is provided a computer-implemented method for controlling dispensing of at least one biologically active agent in intermittent doses over discrete predefined time periods, comprising the steps of: (i) initiating the dispensing of the biologically active agent in intermittent doses at a first background dosage rate; and (ii) adjusting to a background dosage rate according to the number of input signals received over each predefined time period from a signalling device.

10 Claims, 3 Drawing Sheets

(51) Int. Cl.
  *G06F 19/00* (2018.01)
  *A61M 5/168* (2006.01)
  *A61M 5/142* (2006.01)

(52) U.S. Cl.
  CPC .......... *G06F 19/00* (2013.01); *G06F 19/3468* (2013.01); *A61M 5/1723* (2013.01); *A61M 2005/14208* (2013.01); *F04C 2270/0421* (2013.01)

(56) References Cited

U.S. PATENT DOCUMENTS

| | | | |
|---|---|---|---|
| 4,280,494 A | | 7/1981 | Cosgrove, Jr. et al. |
| 5,069,668 A | * | 12/1991 | Boydman ............. A61M 5/172 604/121 |
| 5,677,290 A | | 10/1997 | Fukunaga |
| 2004/0193328 A1 | | 9/2004 | Zaitsu et al. |
| 2005/0277911 A1 | * | 12/2005 | Stewart ............. A61M 5/14228 604/890.1 |

OTHER PUBLICATIONS

Supplementary European Search Report, dated Jul. 28, 2015, for corresponding European Application No. 12 85 5068, 3 pages.
Leo et al., "A randomized comparison of automated intermittent mandatory boluses with basal infusion in combination with patient-controlled epidural analgesia for labor delivery." *International Journal of Obstetric Anesthesia* 19(4): 357-54, 2010. (Abstract Only).
McLintock, "Patient-controlled analgesia," *Intensive Care Nursing* 3(1): 8-13, 1987.
Rudolph et al., "Pain Relief Using Smart Technology: An Overview of a New Patient-Controlled Analgesia Device," *IEEE Transactions on Information Technology in Biomedicine* 3(1): 20-27, 1999.
Sia et al., "Computer-integrated patient-controlled epidural analgesia: a preliminary study on a novel approach of providing pain relief in labour," *Singapore Med J* 47(11): 951-956, 2006.
Boselli et al., "Background Infusion Is Not Beneficial during Labor Patient-controlled Analgesia with 0.1% Ropivacaine plus 0.5 µg/ml Sufentanil," *Anesthesiology* 100(4):968-972, Apr. 2004.
Boutros et al., "Comparison of intermittent epidural bolus, continuous epidural infusion and patient controlled-epidural analgesia during labor," *International Journal of Obstetric Anesthesia* 8:236-241, 1999.
Bremerich et al., "Comparison of continuous background infusion plus demand dose and demand-only parturient-controlled epidural analgesia (PCEA) using ropivacaine combined with sufentanil for labor and delivery," *International Journal of Obstetric Anesthesia* 14:114-120, 2005.
D'Angelo, "New Techniques for Labor Analgesia: PCEA and CSE," *Clinical Obstetrics and Gynecology* 46(3):623-632, Sep. 2003.
Ferrante et al., "The Role of Continuous Background Infusions in Patient-Controlled Epidural Analgesia for Labor and Delivery," *Anesth Analg* 79:80-84, 1994.
Missant et al., "Patient-controlled Epidural Analgesia Following Combined Spinal-epidural Analgesia in Labour: the Effects of Adding a Continuous Epidural Infusion," *Anaesth Intensive Care* 33:452-456, 2005.
Petry et al., "Epidural PCA with bupivacaine 0.125%, sufentanil 0.75µg and epinephrine 1/800.000 for labor analgesia: is a background infusion beneficial?" *Acta Anaesth. Belg.* 51:163-166, 2000.
Van der Vyver et al., "Patient-controlled epidural analgesia versus continuous infusion for labour analgesia: a meta-analysis," *British Journal of Anaesthesia* 89(3):459-465, 2002.

\* cited by examiner

Stage 0, 5ml Bolus in 60 mins, main timer = 60mins
Stage 1, 5ml Bolus at 30mins, main timer = 30mins (or 60mins)
Stage 2, 5ml Bolus at 30mins and 60mins, main timer = 60mins
Stage 3, 5ml Bolus at 20min, 40mins and 60mins, main timer = 60mins
Stage 4, 5ml Bolus at 15mins, 30mins, 45mins and 60mins, main timer = 60mins

COMPUTER-IMPLEMENTED METHOD FOR CONTROLLING DISPENSING OF A BIOLOGICALLY ACTIVE AGENT; COMPUTER SYSTEM AND SOFTWARE THEREOF

FIELD OF THE INVENTION

The field of the invention relates to controlling dispensing of a biologically active agent. In particular, the present invention relates to a computer-implemented method for controlling the dispensing of a biologically active agent; and a computer system programmed to perform the method and software thereof.

BACKGROUND TO THE INVENTION

A conventional mode of labour drug delivery takes the form of constant background infusion, where labour drug is administered to a parturient at a constant rate. However, studies have shown that a constant background infusion of labour drug may not be ideal, as it is not responsive to the dynamic and progressive nature of labour pain. In particular, there have been conflicting results in literature with regard to the merit of administering a basal infusion as well as its optimal infusion rate[4-8].

Patient-Controlled Epidural Analgesia (PCEA) is a mode of labour epidural drug delivery which confers greater autonomy and flexibility by enabling the parturient to self-administer boluses of epidural solution as she deems necessary. Several studies have affirmed the advantages of PCEA over conventional epidural infusion and it has become established as a safe and efficacious mode of labour epidural drug delivery[1-3]. However, despite extensive research over the last decade, the optimal PCEA program settings have not been elucidated.

SUMMARY OF THE INVENTION

According to the present invention, there is provided a computer-implemented method for controlling dispensing of at least one biologically active agent in intermittent doses over discrete predefined time periods, comprising the steps of: (i) initiating the dispensing of the biologically active agent in intermittent doses at a first background dosage rate; and (ii) adjusting to a background dosage rate according to the number of input signals received over each predefined time period from a signalling device.

There is also provided a computer-implemented method for controlled administration of at least one biologically active agent to a subject, comprising the steps of: (i) initiating the dispensing of the biologically active agent in intermittent doses for administration to the subject at a first background dosage rate; and (ii) adjusting to a background dosage rate according to the number of input signals received over each predefined time period from a signalling device.

There is further provided a software executable by a computer system to cause the computer system to perform the method according to the present invention, and a computer program product comprising said software.

There is also provided a computer system, programmed to perform the method according to the present invention.

A more complete understanding of the present invention, as well as further features and advantages of the present invention, will become apparent from the detailed description and figures.

BRIEF DESCRIPTION OF THE FIGURES

Reference numerals indicated in the drawings and referred to in the detailed description are intended for illustrative purposes only and should not be construed as limited to the particular structure indicated in the drawings.

Figure 1:
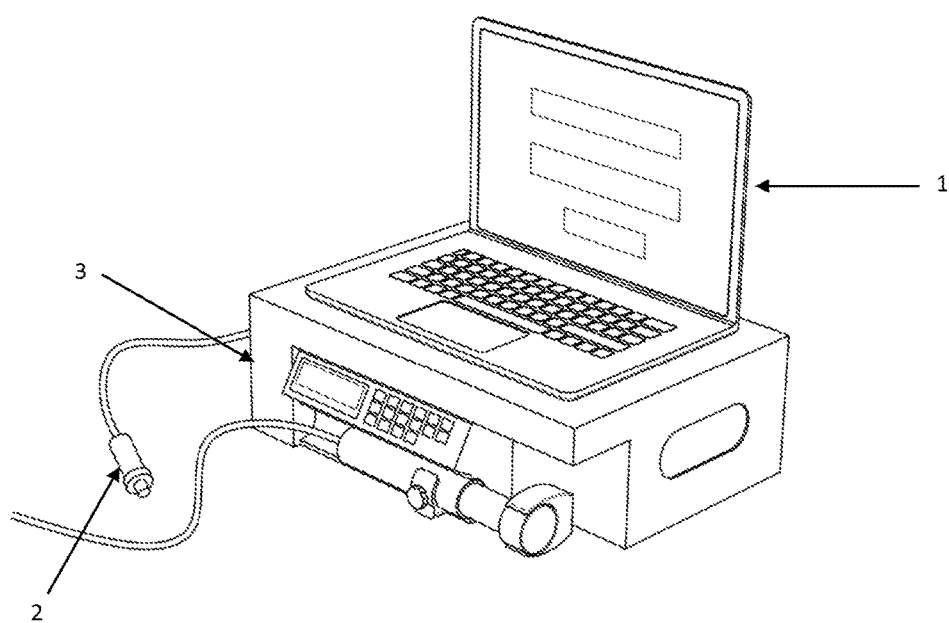
FIG. 1 shows an exemplary delivery system utilizing a computer system 1 (e.g. WIFI enabled notebook such as Hewlett Packard Compaq Tablet PC) connected to a signalling device 2 (push-button type switch or patient demand button"). Program source codes for both the vAMB and PCEA5 regimens are loaded into the computer system.

Mixed model repeated measurement analysis did not detect any difference in post-block serial pain scores between the two groups. A computer-implemented method for controlling dispensing of a biologically active agent according to any aspect of the invention, a computer system programmed to perform the method and software thereof is described in more detail herein.

The invention may be expressed in terms of a method implemented using a computer, or alternatively as a computer system programmed to implement the method, or alternatively as a computer program product (e.g. embodied in a tangible recording, storage medium and/or a computer readable medium) including program instructions which are operable by the computer to perform the method.

According to a first aspect, the computer-implemented method for controlling dispensing of at least one biologically active agent in intermittent doses over discrete predefined time periods comprises the steps of:
 (i) initiating the dispensing of the biologically active agent in intermittent doses at a first background dosage rate
 (ii) adjusting to a background dosage rate according to the number of input signals received over each predefined time period from a signaling device.

The biologically active agent may be for use in administering to a subject. For example, the biologically active agent is for use in epidural administration to a subject.

Accordingly, in a second aspect, there is also provided a computer-implemented method for controlled administration of at least one biologically active agent to a subject, comprising the steps of:
 (i) initiating the dispensing of the biologically active agent in intermittent doses for administration to the subject at a first background dosage rate; and
 (ii) adjusting to a background dosage rate according to the number of input signals received over each predefined time period from a signalling device.

The input signals may be controlled by a user operating the signaling device. In particular, the signaling device may comprise a button which the user can press to inflict an input signal. Typically, the input signal is generated by a user operating the signalling device. In particular, the signalling device is typically connected to the computer system which receives the input signals over a predefined period, which in turn controls dispensing of the biological agent, as discussed further below. Any suitable signalling device is applicable for the method of the present invention. For example, the signalling device may be in the form of a push-button type switch which the user presses to generate the signal. Alternatively, the signaling device may be in the form of a knob which the user turns to generate the signal. The signalling device may be connected to the computer system by any suitable means. For example, the signalling device may be connected to the computer system via cables and/or wireless connection. Wireless connection includes but is not limited to Wi-Fi and/or Bluetooth.

In particular, the method is suitable for administration of a biological agent to a subject. The user generating the input signal may be the subject who is responsible for self-administration of the biological agent according to need. Alternatively, the user generating the input signal may be a third party dispensing the biological agent for delivery to the subject. Such a third party user may generate the input signal as directed by the subject or based on observing the need of the subject.

The method automatically dispenses an intermittent dose of the biological agent over each predefined time period. The intermittent dose may be any suitable dose. For example, the intermittent dose may be 5 ml every 60 mins. The background dosage rate is calculated based on the automated intermittent doses; e.g. for an intermittent dose of 5 ml every 60 min, the background dosage rate is 5 ml/hr.

The first background dosage rate may be any suitable background dosage rate. For example, the first background dosage rate includes but is not limited to 1 ml/h, 2 ml/h, 3 ml/h, 4 ml/h, 5 ml/h, 6 ml/h, 7 ml/h, 8 ml/h, 9 ml/h, 10 ml/h, 11 ml/h, 12 ml/h, 13 ml/h, 14 ml/h, 15 ml/h, 16 ml/h, 17 ml/h, 18 ml/h, 19 ml/h, 20 ml/h. In particular, the first background dosage rate may be 5 ml/h.

The predefined time period may be any suitable time period. The predefined time period may range between 1 to 60 mins. For example, the predefined time period may be 3 mins, 5 mins, 10 mins, 15 mins, 20 mins, 25 mins, 30 mins, 35 mins, 40 mins, 45 mins, 50 mins, 55 mins or 60 mins. In particular, the predefined time period may be 60 mins.

As described, the background dosage rate is adjusted according to the number of input signals received over each predefined time period from the signaling device. For example, if the frequency of the input signals increases, the background dosage rate is increased. For instance, if two input signals are received within the first predefined time period of 60 mins, the automated intermittent dispensing of the biological agent may be adjusted to 5 ml doses every 30 mins for the next predefined period of 60 mins; and the adjusted background dosage rate is 10 ml/h. On the other hand, if the frequency of the input signals decreases, the background dosage rate is decreased.

The method may further comprise additionally dispensing a signal-induced dose of the biologically active agent in response to an input signal from a signaling device. As an example, if an input signal is received, a first signal-induced dose (e.g. 5 ml) of the biological agent is dispensed. This dose may be dispensed substantially immediately or after a time period (for example 30 mins) after the signal. If the first background dosage rate is 5 ml/h, the next automated intermittent 5 ml dose is dispensed 60 mins after the signal-induced dose (background rate 5 ml/h). If a second signal is received over the predefined period of 1 h, a second signal-induced dose is dispensed. The next automated intermittent dose may be adjusted to 5 ml every 30 mins, (background dosage rate of 10 ml/h). If no input signals is received (frequency of input signals decreases), the background dosage rate is adjusted down.

The background dosage rate is continuously adjusted over predefined time periods for the entire duration of dispensing. The background dosage rate over any subsequent predefined time period may return to the same background dosage rate of a previous predefined time period, and even to the initial background dosage rate.

The input signal includes a signal to dispense a signal-induced dose of the biologically active agent and also to adjust the background dosage rate. The overall dosage rate of the biological agent over a predefined time period takes into account the background dosage rate (of the intermittent doses) and the signal-induce doses.

The method according to the invention may further comprise applying a lockout time period after dispensing each intermittent dose and/or signal-induced dose wherein no further signal-induced and/or intermittent doses of the biologically active agent are dispensed. According to another example, the method may further comprise applying a lockout time period after dispensing each intermittent dose and/or signal-induced dose wherein no further signal-induced doses of the biologically active agent are dispensed. This lockout time period is a safety feature. Any suitable lockout time period may be applied. For example, the lockout time period includes but is not limited to 5 mins, 10 mins, 20 mins, 30 mins or 1 h. For example, the lockout period may be 10 mins.

The method may further include the step of generating a signal if the number of input signals received from the signaling device exceeds a predefined number. In particular, the signal may be an alarm or a blinking light. The predefined number of input signals may be more than or equal to 3. More in particular, the predefined number of signals may be more than or equal to 4.

The method according to the present invention may further comprise the step of capping the background dosage rate of the intermittent doses and/or the signal-induced doses at a predefined maximum rate. This is another safety feature. Any suitable predefined maximum rate may be applied. The predefined maximum rate includes but is not limited to 5 ml/hr, 10 ml/hr, 15 ml/hr, 20 ml/hr, 25 ml/hr or 30 ml/hr. For example, the predefined maximum rate may be 20 ml/hr. Capping the background dosage rate of the intermittent doses and the signal-induced doses is equivalent to capping the overall maximum dosage rate.

The parameters of initial background dosage rate, each adjusted background dosage rate, predefined time period, signal-induced dose, lockout time period, predefined number of input signal triggering a signal (e.g. alarm), predefined maximum overall dosage rate may be adapted depending on specific requirements. The biologically active agent used plays an important role in determining these parameters. The method according to any aspect of the invention further includes utilizing at least one dispensing device for dispensing the biologically active agent. Any suitable dispensing device is applicable. For example, the dispensing device comprises a pump and/or a syringe.

The invention also includes a computer system, programmed to perform the method of the present invention. The computer system may in principle be any general computer, such as a personal computer, a laptop, a notebook, a tablet computer, a workstation or a mainframe supercomputer. The computer system may be enabled for wireless communication and/or connection. For example, the computer system may be WI-FI and/or Bluetooth enabled.

The computer system is operatively connected to the dispensing device. The computer system may be connected to the dispensing device by any suitable means. For example, the computer system may be connected to the dispensing device via cables and/or wireless connection. Wireless connection includes but is not limited to Wi-Fi and/or Bluetooth.

Accordingly, there is provided a dispensing system comprising a computer system operatively connected to at least one dispensing device, wherein the dispensing system is configured to perform the method of the present invention.

Figure 2:
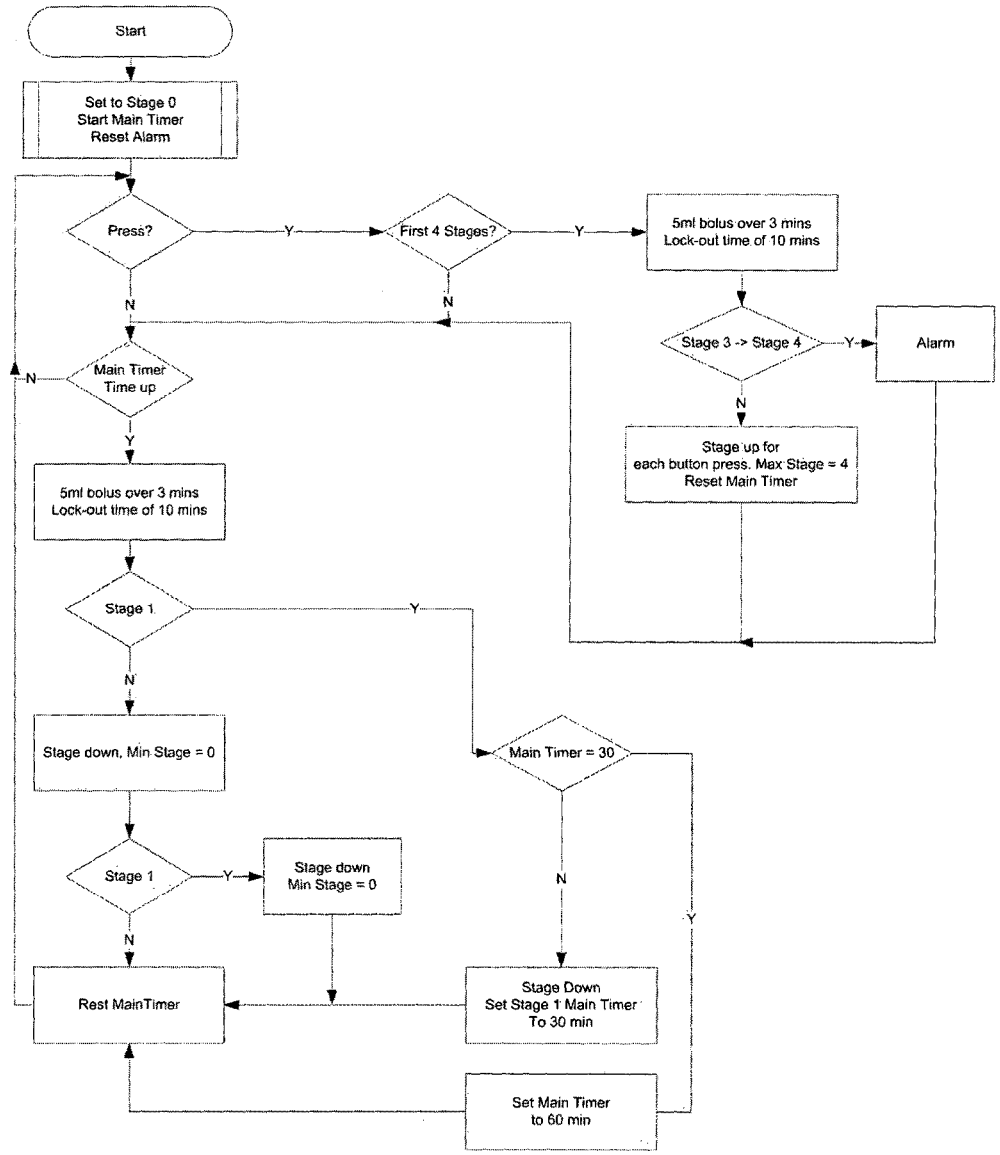
FIG. 2 is a flow chart showing the variable-frequency automated mandatory boluses (vAMB) algorithm of the present invention.

There is also provided a software executable by a computer system to cause the computer system to perform the method according to any aspect of the present invention. The software comprises an algorithm, the variable-frequency automated mandatory boluses (vAMB) algorithm. An example of the vAMB algorithm is shown in FIG. 2.

Further provided a computer program product comprising a software executable by a computer system to cause the computer system to perform the method according to any aspect of the present invention. The computer program product according to an aspect of the invention may comprise a tangible computer program product. In particular, the tangible computer product may comprise a tangible recording, storage and/or computer-readable media. The Invention is suitable for the delivery and/or administration of any suitable biological agent to a subject. For example, the biological agent may comprise an analgesic or an anesthetic. Any route of administration is applicable. For example, the administration comprises epidural administration. In particular, the invention is suitable for labour drug delivery to parturient. The invention is particularly suitable for combined spinal-epidural analgesia. As additional examples, the biologically active agent includes but is not limited to ropivacaine, fentanyl, lidocaine, and the like.

Having now generally described the invention, the same will be more readily understood through reference to the following examples which are provided by way of illustration, and are not intended to be limiting of the present invention.

EXAMPLES

This study compares administering variable-frequency automated boluses at a rate proportional to the patient's needs, in place of a fixed continuous basal infusion in a PCEA regimen. A complex software program which enables an ordinary syringe pump to function as a PCEA pump with the ability to deliver variable-frequency automated mandatory boluses (vAMB) in addition to patient-driven PCEA boluses (FIG. 1) was designed. This program was compared with a conventional PCEA with a basal infusion of 5 mL/h which is the standard regimen used at our institution. The primary outcome of interest was the incidence of breakthrough pain requiring anesthesiologist supplementation.

This study was conducted with the approval of the hospital ethics committee and written informed consent was obtained from every parturient who participated in the study. We recruited 102 healthy (American Society of Anesthesiology Classification ASA I) nulliparous parturients with term gestations (defined as >36 weeks of gestation) and singleton fetus, who were in early labour (cervical dilation <5 cm) and who had requested labour epidural analgesia.

Parturients with multiple pregnancies, non-cephalic presentations, and obstetric complications (e.g. pre-eclampsia and premature rupture of amniotic membranes) were excluded from our study. Parturients who had contraindications to neuraxial blockade or who had received parenteral opioids within the last 2 hours were also excluded.

After establishing intravenous access, a non-invasive blood pressure monitor cuff (Dinamap, Critikon, Fla.) was applied over the parturient's right brachial artery. Baseline systolic blood pressure and heart rate were measured in the supine position with left uterine displacement. Each parturient was pre-loaded with 500 ml of IV Ringer's Lactate solution. A baseline visual analog pain score (VAS) based on a 0-10 cm scale was obtained from the parturient during a uterine contraction, and only those who had a VAS >3 cm were recruited into the study. Pre-block data such as the cervical dilatation prior to neuraxial blockade, use of cervical prostaglandin E2 for induction of labour, artificial rupture of membranes and administration of IV oxytocin for labour augmentation were recorded.

Combined spinal-epidural (CSE) analgesia was explained to each parturient and informed consent obtained as per institution protocol. All neuraxial blocks were performed by a single operator at the L3-4 interspace using the needle-through-needle technique with the patient sitting up. The epidural space was located with an 18-gauge Tuohy needle (Espocan, B. Braun, Melsungen, Germany) using loss of resistance to <2 ml of saline. A 27-gauge pencil point needle was then used to puncture the dura mater and free flow of cerebrospinal fluid (CSF) was confirmed before a standardized intrathecal dose of ropivacaine 2 mg (Naropin, Astra Zeneca, Södertälje, Sweden) and fentanyl 15 µg (David Bull Laboratories, Melbourne, Australia) was injected over 15 seconds with the needle orifice facing cephalad. A multiorifice catheter (Perifix®, B. Braun, Melsungen, Germany) was inserted into the epidural space up to a length of 4 cm in-situ. A test dose of 3 ml of 1.5% lidocaine (Xylocalne, Astra Zeneca, Södertälje, Sweden) was administered through the catheter following negative aspiration for blood and CSF. The patient was then placed supine with left lateral uterine displacement and post-block profile was recorded. If a profound motor block (defined as an inability to flex either knee) or significant hypotension (a reduction of systolic blood pressure >30%) developed within the next 15 mins, the patient would be withdrawn from the study due to suspected intrathecal catheter misplacement. Patients with recognised accidental dural punctures, intravascular catheter placement and those in whom there was a failed spinal (defined as failure to obtain cerebrospinal fluid backflow following two dural punctures with the spinal needle), were also excluded from the study and managed according to departmental protocols.

The parturients were randomly allocated into two groups using sealed opaque envelopes and computer-generated random number tables by an independent assistant, who then programmed the epidural drug delivery system according to group assignment. The parturients were subsequently monitored by a second anesthesiologist who was not involved in performing the block. Neither the parturients nor the anesthesiologists who recorded the post-block data were aware of their group assignment.

The parturients were randomized to receive 0.1% ropivacaine+fentanyl 2 µg/ml via one of the following regimens for maintenance of labour epidural analgesia:

1. PCEA with basal continuous infusion (Group PCEA5): PCEA with basal infusion 5 ml/h initiated immediately following intrathecal drug administration (noted as Time 0). PCEA self-bolus was set at 5 ml, lockout interval at 10 min and maximal dose at 20 ml/h (inclusive of background infusion).

2. PCEA with variable automated mandatory boluses (Group vAMB): PCEA vAMB algorithm as illustrated in FIG. 2, initiated immediately after completion of CSE. This pump was designed to administer intermittent machine boluses of 5 ml in addition to the patient-controlled boluses. The frequency of such automated machine boluses (AMB) would be dependent on the history of the patient's analgesic requirement over the past hour. The first AMB dose was programmed to be delivered 60 min from Time 0 and every hour thereafter if no PCEA patient-bolus were made (background rate 5 ml/h). At the first activation of a PCEA patient-bolus, the timer would be reset with the subsequent AMB delivered 30 min following the PCEA patient-bolus, and every hour thereafter if no further PCEA patient-bolus were made (background rate 5 ml/h). If there was a second PCEA patient-bolus in that same hour, the time interval between two AMB would be shortened to 30 min (background rate 10 ml/h). If there was a third PCEA patient-bolus within that hour, the AMB would be delivered at 20 min intervals (background rate 15 ml/h). A fourth PCEA patient-bolus within the same hour would further shorten the time interval between two AMBs to 15 min (background rate 20 ml/h). On the other hand, if there were no patient-bolus for, the whole of 60 min, the frequency of AMB boluses would step down in the reverse fashion. The lockout period for both PCEA and AMB boluses was 10 min. If a PCEA demand was made within 10 min of an AMB dose, no patient-bolus would be given and this would be recorded as an unsuccessful PCEA attempt. PCEA bolus was set at 5 ml and the maximal hourly limit was set at 20 ml/h (inclusive of automated boluses).

In one example, the AMB would be delivered during the lockout period of the patient's bolus because AMB is considered as the 'background rate'; however, if the AMB is scheduled to substantially coincide with the time of the patient's bolus, then no further AMB will be given at that point in time.

Our institution collaborated with computer engineers to create a software program that allows an ordinary syringe driver to function as a PCEA, with the ability to deliver background mandatory boluses in addition to patient-demand boluses. An epidural drug delivery system utilizing a Hewlett Packard Compaq 2710p Tablet PC operating on Microsoft Windows XP Tablet PC Edition 2005 (Microsoft, USA) connected to a modified B. Braun Perfusor® Compact S infusion pump (B. Braun, Melsungen, Germany) was developed (FIG. 1). Program source codes for both the vAMB and PCEA5 regimens were loaded into the Tablet PC. The two-way communication between the pump and the HP Tablet PC was accomplished by connecting the pump serial ports to the USB port on the Tablet PC. The 5 ml automated machine-boluses as well as PCEA patient-boluses were time-cycled, based on an infusion rate of 100 ml/h and required three minutes to complete. Both programs underwent rigorous in-vitro testing at our institution's Biomedical Engineering Unit and by all investigators independently before being applied to patients in a clinical setting.

Once the parturient reported a VAS <3 cm 15 min after CSE, she would be given a hand-held device and instructed to self-administer a PCEA bolus by pressing the button on the device once she experienced a recurrence of pain. She would be counselled to activate the PCEA bolus even if the pain was only mild, before it increased in severity. She would also be informed about the purpose of a lockout period and maximal hourly dose limit. Parturients who did not obtain satisfactory pain relief (defined as VAS <3 cm) 15 min after CSE were deemed to have an ineffective spinal. The epidural catheter would then be used to administer rescue analgesia and the patient removed from the study.

The following parameters were monitored by an independent anesthesiologist after the block:
1. Systolic blood pressure and heart rate every 5 min for the first 30 min and subsequently at 2 h intervals until delivery
2. Continuous fetal heart rate monitoring
3. VAS 15 and 30 min from Time 0 and subsequently at 2 h intervals until delivery
4. Sensory block height (loss of cold sensation to ice tested at the mid-clavicular line bilaterally) 15 and 30 min from Time 0 and subsequently at 2 h intervals until delivery
5. Degree of lower limb motor blockade 15 and 30 min from Time 0 and subsequently at 2 h intervals until delivery, based on the modified Bromage scale (0=no motor block, 1=unable to flex either hip but able to move knee and ankle joints, 2=unable to flex hip and knee joint of either limb but able to move ankle joints, 3=unable to move hip, knee or ankle joint of either limb)
6. Post-block side effects such as shivering, nausea, vomiting, pruritus, maternal pyrexia, significant maternal hypotension (defined as systolic BP <90 mmHg or >25% decrease from baseline) and fetal bradycardia requiring review by an independent obstetrician. Treatment for maternal hypotension and fetal bradycardia was administered as per institution protocol i.e. IV ephedrine in 5 mg aliquots if maternal hypotension was present, and IV terbutaline 0.25 mg if uterine hyperstimulation was diagnosed.
7. Time of first patient-activated PCEA demand-bolus.

The parturients were instructed to inform the attending anesthesiologist if they experienced inadequate pain relief (VAS 3 cm or more) whilst on PCEA therapy. Additional pain relief would then be administered by the anesthesiologist via the indwelling epidural catheter and this would constitute an episode of breakthrough pain. According to departmental guidelines, the attending anesthesiologist would administer epidural 0.2% ropivacaine in 5 ml aliquots every 10 min (up to a maximum of 20 ml) until VAS <3 cm. Fentanyl 50 mcg was added if VAS remained ≥3 cm after 10 ml of epidural 0.2% ropivacaine had been given. The pumps were paused for the duration of time taken to administer each clinician bolus, and resumed immediately after. Such clinician-administered manual boluses did not affect the PCEA pump settings in any way. The episode of breakthrough pain was concluded once the parturient reported a VAS <3 cm. The following data was recorded at each episode of breakthrough pain: time of occurrence, pain scores, cervical dilation, use of oxytocin and total dose of epidural medication needed to abolish the pain. If the epidural top-up failed to achieve adequate analgesia (defined as VAS <3 cm), the catheter was deemed ineffective and the parturient would also be removed from the study.

Obstetrical and neonatal outcomes such as mode of delivery (vaginal, instrumental or cesarean delivery), indication for instrumental or cesarean delivery, duration of second stage of labour and neonatal Apgar scores at 1 and 5 min were noted. The parturient would be interviewed within 24 h of delivery by a separate anesthesiologist not involved in the study for an overall assessment of her satisfaction with labour analgesia (graded on a verbal scale from 0 to 100, with 0 being very dissatisfied and 100 being extremely satisfied).

A sample size of 49 patients in each group was required to detect a 20% reduction in the incidence of breakthrough pain requiring physician top-up for patients in the vAMB arm compared with those in the PCEA5 arm ($\alpha=0.05$, $\beta=0.2$). A reduction in the incidence of breakthrough pain from a baseline of 25% at our institution to 5% was deemed clinically significant, as this could potentially improve patient satisfaction and reduce clinician workload in a busy obstetric unit like ours. All data and statistical analyses were managed with SPSS version 15 (SPSS Inc., Chicago, Ill., USA). The Student's t-test was used for the analysis of continuous data that was normally distributed and the Mann Whitney test employed for nonparametric data. For categorical data and proportions, the $\chi 2$ test with Yates correction (where appropriate) was applied. Kaplan Meier survival analysis was used to compare the duration of effective analgesia after CSE prior to the first episode of breakthrough pain requiring epidural top-up by an anaesthesiologist (if any). If the parturient delivered without experiencing breakthrough pain, the interval from Time 0 to delivery was computed as the censored data in the eventual Kaplan Maier analysis. The mean survival times to the first episode of breakthrough pain were analyzed using the log rank test.

For analysis of serial measurements such as pain scores and sensory levels, the Mixed Model repeated measurement analysis technique was employed to adjust for missing data at time intervals after the parturients had delivered and the epidural infusion had been stopped.

All 102 recruited parturients completed the study. Baseline demographic and pre-block obstetric data were similar for parturients in both groups (Table 1). None of the patients had a failed spinal or an ineffective epidural catheter. There were no patients who had inadvertent intravascular catheter misplacement or accidental dural puncture.

TABLE 1

Patient's baseline demographic and preblock obstetric data

|  | VAMB (N = 51) | PCEA5 (N = 51) | P-VALUE |
|---|---|---|---|
| BMI (kg/m$^2$) | 27.3 (3.9) | 28.2 (4.9) | 0.32 |
| Cervical dilatation preblock (cm) | 3.2 (0.7) | 3.2 (0.9) | 0.86 |
| Maternal systolic BP (mmHg) | 113.8 (10.6) | 115.9 (11.9) | 0.35 |
| Maternal diastolic BP (mmHg) | 67.8 (9.5) | 68.4 (9.3) | 0.76 |
| Maternal heart rate (bpm) | 76.0 (10.1) | 79.2 (13.2) | 0.18 |
| Fetal heart rate (bpm) | 139.4 (10.1) | 141.2 (11.1) | 0.38 |
| Preblock VAS (cm) | 8.0 (1.7) | 7.8 (1.5) | 0.62 |
| Preblock use of Entonox | 28 (55.0%) | 24 (47.1%) | 0.55 |
| Preblock pethidine (>2 hr ago) | 4 (7.8%) | 6 (11.8%) | 0.74 |
| Preblock use of oxytocin | 18 (35.3%) | 14 (27.5%) | 0.52 |
| Preblock use of Prostin | 23 (45.1%) | 20 (39.2%) | 0.69 |
| Preblock Artificial Rupture of Membranes | 33 (64.7%) | 28 (54.9%) | 0.42 |

Values are n (%) or mean (SD)

Figure 3:
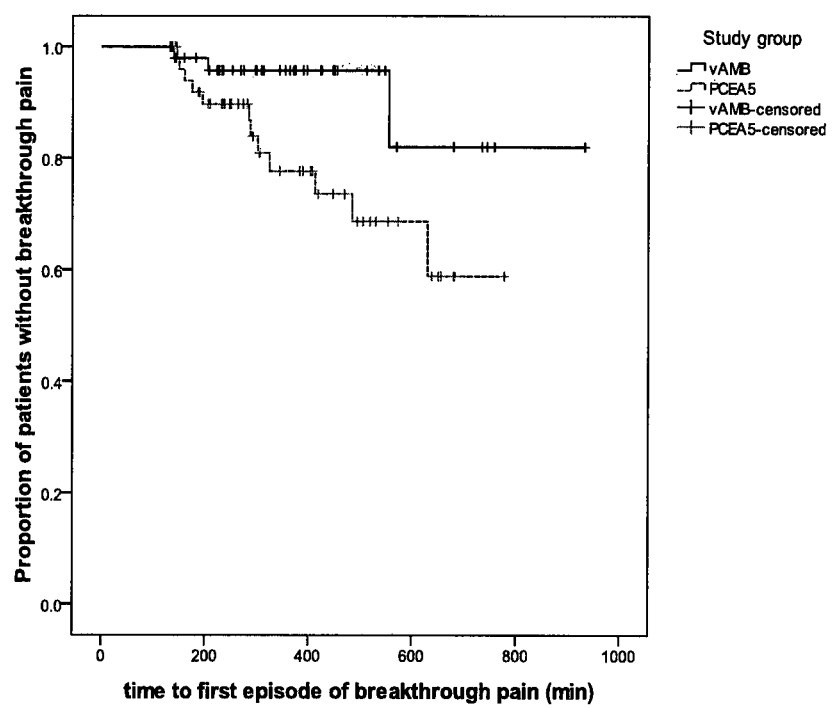
FIG. 3 is a graph showing the time to the first episode of breakthrough pain for the vAMB and PCEA 5 study groups. The mean survival time before first episode of breakthrough pain was 849.9 min (Standard Deviation; SD=52.2) in Group vAMB and 613.1 min (SD=39.2) in group PCEA5 taking into account patients who delivered without experiencing breakthrough pain as censored data (p=0.028 by log rank test).

The incidence of breakthrough pain requiring epidural top-up by an attending anesthesiologist was significantly lower in the vAMB group (3 patients [5.9%]) compared to the PCEA5 group (12 patients [23.5%]); (p=0.023). There were two patients in the PCEA5 group who experienced two episodes of breakthrough pain. Patient profiles at the time of breakthrough pain are shown in Table 2 and mean survival times prior to first breakthrough pain illustrated in FIG. 3.

TABLE 2

Patient profile at breakthrough pain

|  | VAMB (N = 3) | PCEA5 (N = 12) | P-VALUE† |
|---|---|---|---|
| Time to 1$^{st}$ breakthrough pain (min) | 299.7 (129.1) | 296.1 (43.5) | 0.99 |
| Volume of epidural solution infused at 1$^{st}$ breakthrough pain (ml) | 35.0 (26.5) | 51.4 (22.2) | 0.25 |
| Cervical dilation at 1$^{st}$ breakthrough pain (cm) | 5.3 (2.1) | 6.6 (2.3) | 0.42 |
| VAS at 1$^{st}$ breakthrough pain (cm) | 6.0 (0) | 7.4 (1.5) | 0.12 |
| Oytocin infusion at 1$^{st}$ breakthrough pain (ml/h) | 24.0 (15.9) | 16.5 (21.4) | 0.30 |
| Sensory level at 1$^{st}$ breakthrough pain | T8 [T6 to T10] | T8 [T6 to T10] | 0.89 |
| Bromage score at 1$^{st}$ breakthrough pain | 0 | 0 | 1.0 |

Values are mean (SD) or median [range]
†Nonparametric tests were applied due to small number of patients with breakthrough pain This improved analgesic efficacy was achieved without any significant difference in the amount of local anesthetics consumed. The time-weighted mean hourly consumption of ropivacaine, inclusive of clinician-administered supplemental boluses, were similar in both groups (10.0 mg [SD 3.0] in the vAMB group versus 11.1 mg (SD 3.2) in the PCEA5 group; p=0.06). There was also no difference in the total amount of ropivacaine used (62.0 mg [SD 32.6] in the vAMB group versus 74.2 mg (SD 34.0) in the PCEA5 group; p=0.07). Time to first patient demand-bolus following CSE was similar (115.8 min [SD 65.2] in the vAMB group versus 112.1 (SD 70.4) in the PCEA5 group; p=0.78).

The mean VAS score following CSE for the vAMB and PCEA5 study groups were monitored for up to 10 h post CSE. Mixed Model repeated measurement analysis did not detect any difference in post-block serial pain scores nor sensory levels between the two groups, although this could be due to the study not being adequately powered for these comparisons. Maternal side effects experienced were also similar in both groups (Table 3). One parturient from Group PCEA5 had hypotension which resolved following administration of IV ephedrine 5 mg bolus. Two patients in Group PCEA5 had fetal bradycardia requiring administration of IV Terbutaline 0.25 mg. Two patients in Group vAMB had fetal bradycardia, with one being resolved spontaneously and the other requiring IV Terbutaline 0.5 mg. None of the four parturients required an emergency cesarean section.

TABLE 3

Side effects of block

|  | VAMB (N = 51) | PCEA5 (N = 51) | P-VALUE |
|---|---|---|---|
| Shivering | 23 (45.1%) | 26 (51.0%) | 0.69 |
| Pruritus | 29 (56.9%) | 27 (52.9%) | 0.84 |
| Nausea | 1 (2.0%) | 1 (2.0%) | 1.0 |
| Vomiting | 1 (2.0%) | 2 (3.9%) | 1.0 |
| Maternal pyrexia | 3 (5.9%) | 4 (7.8%) | 1.0 |
| Maternal hypotension | 0 | 1 (2.0%) | 1.0 |
| Fetal bradycardia | 2 (3.9%) | 2 (3.9%) | 1.0 |

Values are n (%)

Parturients in both groups had similar mean durations of labour. There was no difference in the duration of the second stage of labour amongst parturients who delivered vaginally, either with or without instrumental assistance. This was in spite of the significantly higher rate of machine-delivered background epidural boluses in Group vAMB [mean 10.9 ml/h (SD 4.5)] compared to the mean background infusion rate of 4.8 ml/h (SD 1.0) in Group PCEA5 at full cervical dilatation (p<0.001). Two parturients in Group PCEA5 had their epidural infusion stopped by the obstetrician during the second stage of labour. Neonatal outcomes such as fetal birthweight and Apgar scores were similar (Table 4).

TABLE 4

Obstetric and Neonatal outcomes

| | VAMB (N = 51) | PCEA5 (N = 51) | P-VALUE |
|---|---|---|---|
| Duration of labour (min) | 389.4 (202.9) | 414.2 (181.3) | 0.52 |
| Duration of 2$^{nd}$ stage (min) | 69.8 (48.9) | 84.9 (57.9) | 0.22 |
| Background epidural maintenance at full cervical dilatation (ml/h) | 10.9 (4.5) | 4.8 (1.0) | <0.001 |
| Mode of delivery | | | |
| Normal Vaginal Delivery | 33 (64.7%) | 32 (62.7%) | 0.65 |
| Instrumental delivery | 5 (9.8%) | 8 (15.7%) | |
| Cesarean delivery | 13 (25.5%) | 11 (21.6%) | |
| Fetal birthweight (g) | 3244.4 (392.5) | 3083.5 (502.9) | 0.08 |
| Neonatal Apgar Scores at 5 min | 9 | 9 | 1.00 |
| Satisfaction Score | 96.5 (5.0) | 89.2 (9.4) | <0.001 |

Values are n (%) or mean (SD)

When asked to rate their overall labour analgesia experience, parturients in Group vAMB reported higher satisfaction scores compared to those in PCEA5 (mean=96.5, SD=5.0 versus mean=89.2, SD=9.4 respectively; p<0.001).

The results demonstrated that using variable-frequency automated intermittent boluses in place of a continuous basal infusion in PCEA for labour analgesia resulted in a reduced incidence of breakthrough pain requiring anesthesiologist supplementation and greater overall maternal satisfaction without any increase in local anesthetic consumption.

The role of a basal infusion in PCEA has long been a topic of debate. On one hand, studies have shown that PCEA with a basal infusion can reduce the incidence of breakthrough pain and reduce pain scores with no increase in local anaesthetic consumption compared to a demand-only PCEA[4-6]. On the other hand, some investigators found that using a basal infusion in a PCEA regimen may increase local anesthetic consumption without improving analgesic efficacy[7,8]. The present invention successfully combines the advantages of administering patient-regulated background epidural infusates in the form of intermittent boluses instead of a fixed continuous basal infusion in a PCEA regimen. Varying the frequency of automated mandatory boluses in tandem with the frequency of patient demand-boluses improves the analgesic efficacy of a PCEA regimen, as shown in the reduced incidence of breakthrough pain requiring supplementation by an anesthesiologist. The lack of difference in local anesthetic consumption between the two groups is likely due to the auto-regulatory feature of the vAMB regimen, which minimizes drug usage in early labour when pain is less intense and allows greater drug consumption to match the escalating pain of advanced labour. Indeed, a significantly higher rate of machine-delivered background epidural boluses in Group vAMB compared to the mean basal infusion rate in Group PCEA5 at full cervical dilatation was found. We postulate that this may have alleviated perineal pain more effectively and thus contributed to the observed increase in maternal satisfaction in Group vAMB. No adverse effects resulting from the higher consumption of local anesthetic during advanced labour were detected, as shown by the duration of second stage, modes of delivery and neonatal outcomes being similar in both groups. Although patient profiles at the first episode of breakthrough pain were largely similar, the number of patients whose data we analyzed was too small to draw any meaningful conclusion.

The results show that variable-frequency automated mandatory boluses are superior to a constant background infusion in PCEA for the maintenance of labour epidural analgesia. A reduction in the need for anesthesiologist-administered supplementation of the epidural block not only increases maternal satisfaction but may also be important in reducing workload at a busy tertiary obstetric unit.

REFERENCES

1. Van der Vyver M, Halpern S, Joseph G. Patient-controlled epidural analgesia versus continuous infusion for labour analgesia: a meta-analysis. Br J Anaesth 2002; 89:459-65.
2. Boutros A, Blary S, Bronchard R, Bonnet F. Comparison of intermittent epidural bolus, continuous epidural infusion and patient controlled-epidural analgesia during labor. Int J Obstet Anesth, 1999; 4: 236-41
3. D'Angelo R. New techniques for labor analgesia: PCEA and CSE. Clin Obstet Gynecol 2003; 46:623-32.
4. Ferrante F M, Rosinia F A, Gordon C, Datta S. The role of continuous background infusions in patient-controlled epidural analgesia for labor and delivery. Anesth Analg 1994; 79:80-84.
5. Missant C, Teunkenst A, Vandermeersch E, Van de Velde M. Patient controlled epidural analgesia following combined spinal-epidural analgesia in labour: the effects of adding a continuous epidural infusion. Anaesth Intensive Care 2005; 33:452-456.
6. Bremerich D H, Waibel H J, Mierdl S, et al. Comparison of continuous background infusion plus demand dose and demand-only parturient-controlled epidural analgesia (PCEA) using ropivacaine combined with sufentanil for labor and delivery. Int J Obstet Anesth 2005; 14:114-120.
7. Petry J, Vercauteren M, Van Mol I, et al. Epidural PCA with bupivacaine 0.125%, sufentanil 0.75 microgram and epinephrine 1/800 000 for labor analgesia: is a background infusion beneficial? Acta Anaesthesiol Belg 2000; 51:163-166.
8. Boselli E, Debon R, Cimino Y, et al. Background infusion is not beneficial during labor patient-controlled analgesia with 0.1% ropivacaine plus 0.5 mg/ml sufentanil. Anesthesiology 2004; 100:968-972.

The invention claimed is:
1. A computer-implemented method for controlling dispensing of at least one biologically active agent in intermittent doses over discrete predefined time periods, comprising the steps of:
 (i) initiating the dispensing of the biologically active agent in the intermittent doses at a first background dosage rate, and setting a first predefined time period; additionally dispensing a first stage signal-induced dose of the biologically active agent, in response to an input signal from a signalling device within the first predefined time period, and setting a second predefined time period;

dispensing a second stage signal-induced doses of the biologically active agent, in response to a second input signals from the signalling device within the second predefined time period, and re-setting the second predefined time period;

dispensing a third stage signal-induced dose of the biologically active agent, in response to a third input signal from the signalling device within the second predefined time period, and re-setting the second predefined time period;

dispensing a fourth stage signal-induced dose of the biologically active agent, in response to a fourth input signal from the signalling device within the second predefined time period, and re-setting the second predefined time period;

preventing further dispensing stages within the second predefined time period, and then; re-setting the second predefined time period.

2. The method according to claim 1, further comprising applying a lockout time period after dispensing each intermittent dose or each signal-induced dose wherein no further of the signal-induced or the intermittent doses of the biologically active agent are dispensed.

3. The method according to claim 1, wherein if the fourth stage input signal is received from the signalling device, an alert signal is generated.

4. The method according to claim 1, further comprising capping the background dosage rate at a predefined maximum rate.

5. The method according to claim 1, wherein the biologically active agent is for use in administering to a subject.

6. The method according to claim 1, wherein the biologically active agent is for use in epidural administration to a subject.

7. The method according to claim 1, further including the step of (ii) adjusting to a background dosage rate according to the number of the input signals received over each predefined time period from the signalling device, wherein step (ii) comprises at least one of:
   (a) increasing the background dosage rate if a frequency of the input signals increases; or
   (b) decreasing the background dosage rate if a frequency of the input signals decreases.

8. A dispensing system comprising a computer system operatively connected to at least one dispensing device, wherein the dispensing system is configured to perform a method for controlling dispensing of at least one biologically active agent in intermittent doses over discrete predefined time periods, comprising the steps of:

initiating the dispensing of the biologically active agent in intermittent doses at a first background dosage rate, and setting a first predefined time period;

additionally dispensing a first stage signal-induced dose of the biologically active agent, in response to an input signal from a signalling device within the first predefined time period, and setting a second predefined time period;

dispensing a second stage signal-induced doses of the biologically active agent, in response to subsequent input signals from the signalling device within the second predefined time period, and re-setting the second predefined time period;

dispensing a third stage signal-induced dose of the biologically active agent, in response to a third input signal from the signalling device within the second predefined time period, and re-setting the second predefined time period;

dispensing a fourth stage signal-induced dose of the biologically active agent, in response to a fourth input signal from the signalling device within the second predefined time period, and re-setting the second predefined time period;

preventing further dispensing stages within the second predefined time period, and then; re-setting the second predefined time period.

9. The dispensing system according to claim 8, wherein the dispensing device comprises either one or both of a pump and a syringe.

10. The dispensing system according to claim 8, wherein the method for controlling dispensing of at least one biologically active agent in intermittent doses over discrete predefined time periods further comprises the step of (ii) adjusting to a background dosage rate according to the number of the input signals received over each predefined time period from the signalling device, wherein step (ii) comprises at least one of:
   (a) increasing the background dosage rate if a frequency of the input signals increases; or
   (b) decreasing the background dosage rate if a frequency of the input signals decreases.

* * * * *